US00PP19899P2

(12) United States Plant Patent
Thomas

(10) Patent No.: US PP19,899 P2
(45) Date of Patent: Apr. 14, 2009

(54) ***AZALEA* PLANT NAMED 'ROBLEO'**

(50) Latin Name: ***Rhododendron* hybrid**
Varietal Denomination: Robleo

(75) Inventor: Amy Duck Thomas, Bokeelia, FL (US)

(73) Assignee: Plant Development Services, Inc., Loxley, AL (US)

( * ) Notice: Subject to any disclaimer, the term of this patent is extended or adjusted under 35 U.S.C. 154(b) by 282 days.

(21) Appl. No.: 11/500,521

(22) Filed: Aug. 8, 2006

(51) Int. Cl.
*A01H 5/00* (2006.01)

(52) U.S. Cl. ..... Plt./239

(58) Field of Classification Search ..... Plt./239
See application file for complete search history.

*Primary Examiner*—Kent Bell
(74) *Attorney, Agent, or Firm*—Breiner & Breiner, LLC

(57) ABSTRACT

A new and distinct variety of *Azalea* plant named 'Robleo', characterized by its unique blooming time, upright dense and globose growth habit, and attractive large semi-double multi-colored flowers.

1 Drawing Sheet

Genus species: *Rhododendron* hybrid.
Varietal denomination: 'Robleo'.

BACKGROUND OF THE INVENTION

The present invention relates to a new and distinct variety of evergreen *azalea* of the genus *Rhododendron* and a member of the Ericaceae family. This new *azalea* variety, hereinafter referred to as 'Robleo', was discovered by Robert Edward Lee in July, 2002 in Independence, La. 'Robleo' originated as a naturally occurring branch sport of *Azalea* hybrid 'Conleo' U.S. Plant Pat. No. 11,640 while it was being grown in Independence, La. The value of this new cultivar lies in its unique blooming period, bloom color, bloom form, bloom size, and growth habit.

Asexual propagation of the new plant by cuttings has been under Mr. Lee's direction at the same location. The new plant retains its distinctive characteristics and reproduces true to type in successive generations. The plant cannot be reproduced true from seed.

SUMMARY OF THE INVENTION

The following are the most outstanding and distinguishing characteristics of this new cultivar when grown under normal horticultural practices in Independence, La.

1. The unique spring, summer, and fall blooming.
2. Attractive pink flower color ranging from Red Group 55D to White Group 155D.
3. Large, semi-double flower with wavy petal margins. The flowers range in size from 2½"–3" in diameter.
4. Easily propagated with semi-hardwood cuttings in late spring through the summer.
5. Fast growth rate under normal fertilization and moisture conditions.
6. Upright, dense and globose in nature.
7. Good specimen plant.
8. Desirable in planters.
9. Makes a very good hedge or screen.
10. Very good foundation plant for large buildings.

11. Does well as an understory plant in a woodland garden.
12. Hardy to Zone 7.
13. Attracts butterflies.

DESCRIPTION OF THE DRAWINGS

This new *Azalea* hybrid variety is illustrated by the accompanying photographic prints in which:

1. The photograph at the top of the sheet is a close-up showing flower, foliage, and stem color as well as flower size and form.
2. The photograph at the bottom shows the dense, upright and globose growth habit of a young three gallon plant.

The colors shown are as true as is reasonably possible to obtain by conventional photographic procedures. Colors in the photographs may appear different than actual colors due to light reflectance. The colors of the various plant parts are defined with reference to The Royal Horticultural Society Colour Chart. Description of colors in ordinary terms is presented where appropriate for clarity in meaning.

BOTANICAL DESCRIPTION OF THE PLANT

The following is a detailed description of the new variety of *Azalea* based on my observations made of two year old plants grown in three gallon containers in wholesale commercial production practices, in greenhouses, and in established landscape plantings in Independence, La.

Distinctive Characteristics:

TABLE 1

| Characteristic | 'Robleo' | 'Conleo' PP #11.640 | *R. oldhamii* 'Fourth of July' | 'May Blaine' |
|---|---|---|---|---|
| Height (Mature) | 5-6' | 5-6' | 8-10' | 3-4' |
| Width (Mature) | 5-6' | 5-6' | 6-7' | 3-4' |
| Flower Size | 2½-3" | 2½-3" | 1¾-2¼" | 2½-3" |
| Flower Form | Semi-double | Semi-Double | Single | Double |

TABLE 1-continued

| Characteristic | 'Robleo' | 'Conleo' PP #11.640 | *R. oldhamii* 'Fourth of July' | 'May Blaine' |
|---|---|---|---|---|
| Flower Color | Red G. 55D-White G. 155D | Red G. 44D | Red G. 39A | Red-Purple G. 73C |
| Flowers per Terminal | 2-4 | 2-4 | 2-4 | 2-3 |
| Bloom Period | April | April | | May |
| Bloom Period | Mid July > Frost | Mid July > /Frost | Mid-June > Frost | |
| Petal/ Petaloid No. | 10-15 | 10-15 | 5 | 12-16 |
| Hardy Zone | 7 | 7 | 7 | 7 |
| Stamen Number | 0-5 | 0-5 | 7-10 | 0-8 |
| Stamen Type | Some Petaloid | Some Petaloid | Non-Petaloid | Some Petaloid |

'Robleo' originated as a branch sport of *Azalea* hybrid 'Conleo' U.S. Plant Pat. No. 11,640 which was the result of Mr. Lee's planned cross hybridization between the *Azalea* 'May Blaine' (unpatented) and *Rhododendron oldhamii* 'Fourth of July' (unpatented). The new variety differs from 'Conleo' in its flower color which is Red Group 55D to White Group 155D rather than Red Group 44D.

Mr. Lee's hybridization program was conducted with emphasis on species that are not commonly found in the genetic make-up of the present day hybrids. The 'Fourth of July' cultivar is a heavy summer and fall blooming plant, not like the *Rhododendron* Species Foundation form. The flower buds form on new growth and start blooming about July 14. Mr. Lee used this cultivar to cross with existing hybrids which have a tendency to bloom in the fall and which are also fairly hardy. As expected, the resulting seedlings are heavy summer and fall bloomers with very impressive spring blooms also.

Classification:

*Botanic.*—*Rhododendron* hybrid 'Robleo'.

*Form.*—Upright, dense, and rounded.

*Height.*—5–6'.

*Width.*—5–6'.

*Growth habit.*—Upright, dense and globose. Fast growth rate under normal fertilization and moisture conditions.

*Growth rate.*—In a period of six years from a rooted cutting the plant reaches a height of 3 feet and a spread of 4 feet. The growth rate is normally about 10 to 12" per year; the plant reaches a height of 5 to 6' at maturity while maintaining a dense habit due to the abundant branch development.

*Foliage.*—Alternate, simple, evergreen, pubescent, elliptic, and varying in size from 1½" to 1⅞" long and ⅝" to 13/16" wide. The margins are entire, with a petiole 3/16" to 5/16" long. Midveins and laterals are impressed on the upper leaf surface and prominent on the underside. The base of the leaf is cuneate to attenuate and the apex is acute to mucronate. The upper surface of the immature leaves are dull, pubescent, and are Yellow-Green Group 144A and the underside is Yellow-Green Group 146D, pubescent, and matte. The upper surface of the mature leaves are Yellow-Green Group 146A, dull and slightly pubescent and the underside is Yellow-Green Group 146C, matte, and pubescent. The immature petioles, midribs, and veins are Yellow-Green Group 146C. New growth is pubescent. These hairs are initially soft and white and cover both sides of the leaf with a higher concentration on the petioles and veins. They are slightly curled, flat, and range in length from 1/32" to ⅛". As the growth matures much of the leaf pubescence is lost; however, the stems, petioles, and leaf veins retain this pubescence which becomes more setaceous and darker in color (Brown Group 200A) through the growing season.

In 2005, the date of initial spring growth was March 8, in Independence, La. After the initial spring flush there was almost continuous growth until that fall ending October 25, also in Independence, La. When grown in full sun, the internode length of this plant is 3/16" to ½", when grown in light shade the internode length is ⅜" to ⅝". As would be expected a plant grown in shade results in a taller, less dense plant with larger leaves.

The average length of terminal growth of the initial spring flush is about 6" for a plant in full sun and about 8" when grown in shade. This growth should not be trimmed since it will produce flowers starting in mid July. As the plant continues to growth through the summer and fall more flower buds are produced, which mature and bloom until frost. This remaining growth produces about 5" to 6" of height. As cool weather approaches, some of the flower buds become dormant. These buds bloom in April of the next year.

Stems: The young stems are Yellow-Green Group 146C and densely clothed with spreading while glandular hairs. During the second growing season they become Greyed-Green Group 197B, glabrous and rugose. The pith is solid and uniform. Young and older stems are densely branched.

Buds: Tight buds at ½" are ovate and acuminate Yellow-Green Group 146D with a hairy pubescence Brown Group 200A. The buds are borne in clusters of 2 to 4, and are sheathed by a pair of modified leaf bracts which are from ¼" to ½" long, persistent, and Yellow-Green Group 147A. The pedicel is ⅜" to ½" long, pubescent, and Red Group 39B. The calyx is ⅛" long, Yellow-Green Group 144B, funnel shaped, persistent, and pubescent. The five imbricated sepals are lanceolate and joined at the base to form a cup. As the buds swell the bud sheath matures to a Greyed-Orange Group 165A, falls off, and reveals the flower color Red Group 55D to White Group 155D.

Flowers: Perfect, semi-double, glabrous, open funnel shaped, 2½" to 3" in diameter by 2" to 2¼" in depth, borne on current season's growth, non-fragrant; they last on the plant in the garden 5 to 6 days. Flower color is mostly Red Group 55D with occasional flowers being partially or wholly White Group 155D. These color designations are for both the upper surface and the undersurface. A plant with these color variations is not fixed except in the sense that it will continue to produce a known range of variants. There are five true petals which are fused at the base, elliptic to obovate, and have wavy margins. These petals are 1½" to 2⅛" long, ⅞" to 1⅛" wide, and have rounded apexes and entire margins. The dorsal lobe and the two upper wings of these true petals are dotted Red Group 53C. There are 0 to 5 non-petaloid stamens which are ¼" to 1" long. The filaments are Red Group 55C, the anthers are Greyed-Orange Group 167B, and the pollen matures to Yellow Group 11B. The 5 to 10 petaloid stamens are from ¾" to 2" long and odd shaped. The uppermost petaloid stamens are dotted Red Group 53C. The pistil is single, non-petaloid, ¾" to 1½" long and Red Group 55B. The ovary is densely glandular-setose and has five locules. The capsule matures in about 5 months, in Independence, La., to about ¼" to ½" long; it has a persistent style, is Yellow-Green Group 147A, and contains from 100 to 400 nonwinged seeds. Normally fruit set is not heavy. There is a 2 to 3 week flowering period in April in Independence, La. Flowering resumes in mid July as the new buds mature and continues until frost which can be as late as November or December in Independence, La. *Azaleas* blooming at this time of year attract butterflies in profusion.

Culture: Grows well in a wide range of conditions, tolerates sun to shade. Prefers a moist, well-drained soil that is rich in organic matter. Responds well to mulching and medium applications of fertilizer; prefers ph 5.0 to 5.5. Very little pruning is needed; adaptable to container and above ground planters; makes a good foundation plant or informal hedge with excellent foliage and flower contrast. Ideal for coastal regions and warmer parts of Piedmont. Propagated with semi-hardwood cuttings in late spring through the summer.

Pests: Lace wing and spider mites can be a problem.

I claim:

1. A new and distinct variety of *Azalea* plant named 'Robleo' as illustrated and described.

* * * * *

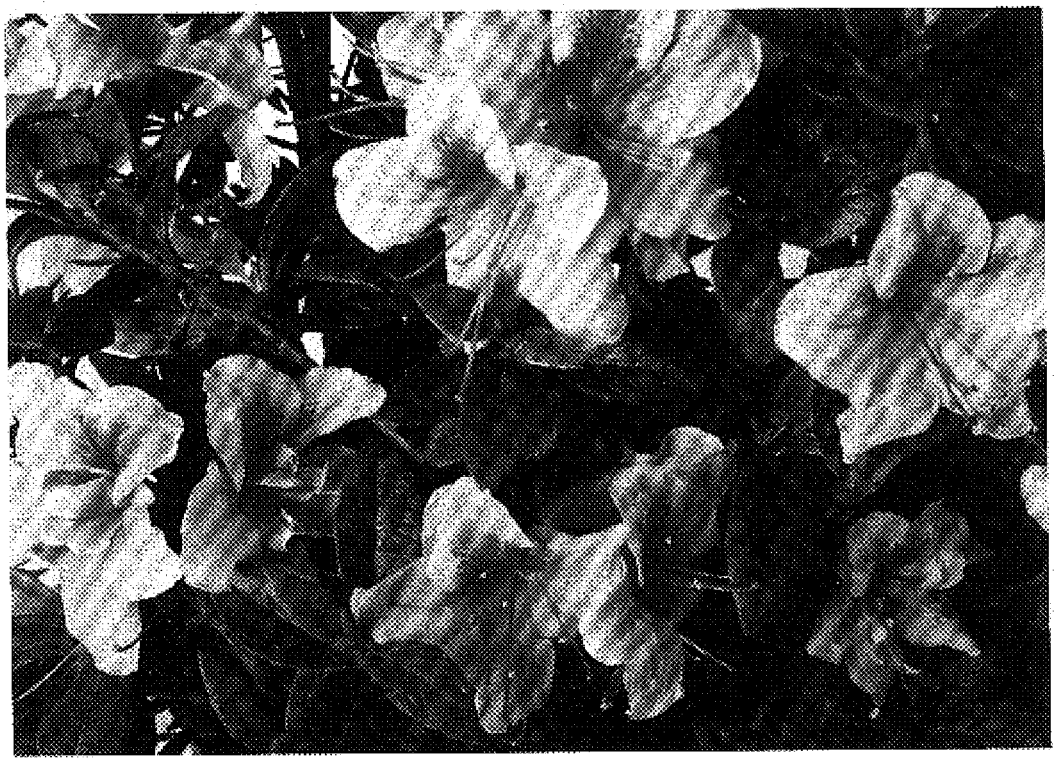
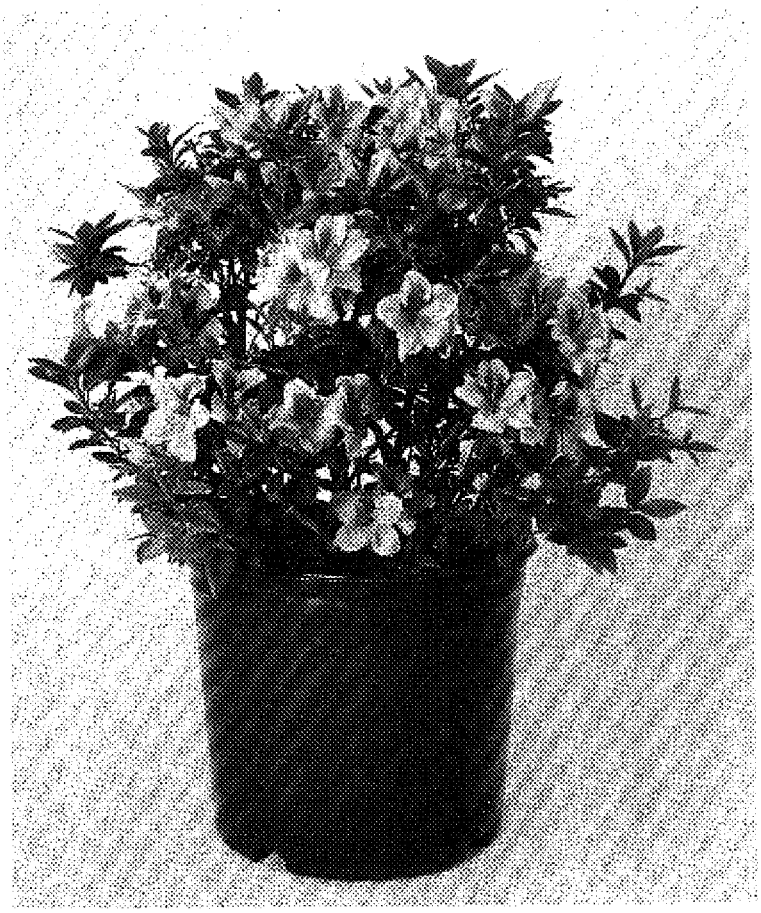

UNITED STATES PATENT AND TRADEMARK OFFICE

CERTIFICATE OF CORRECTION

PATENT NO. : PP 19,899 P2
APPLICATION NO. : 11/500521
DATED : April 14, 2009
INVENTOR(S) : Amy Duck Thomas It is certified that error appears in the above-identified patent and that said Letters Patent is hereby corrected as shown below:

Column 1,
Lines 6-15 (entire paragraph), should read

-- The present invention relates to a new and distinct variety of evergreen *azalea* of the genus *Rhododendron* and a member of the Ericaceae family. This new *azalea* variety, hereinafter referred to as 'Robleo', originated as a naturally occurring branch sport of *Azalea* hybrid 'Conleo' U.S. Plant Patent No. 11,640 while it was being grown in Loxley, AL. 'Conleo' is a new and distinct *azalea* hybrid variety plant discovered by Robert Edward Lee in Independence, LA. 'Conleo' was transported to Loxley, AL as an extension of Mr. Lee's hybridization program. In furtherance of this hybridization program, 'Robleo' was discovered by Amy Duck Thomas in July 2002 in Loxley, AL. (Mr. Lee's breeding program in Independence, LA and Loxley, AL is collectively referred to hereinafter as Independence, LA.) The value of this new cultivar lies in its unique blooming period, bloom color, bloom form, bloom size, and growth habit. --.

Column 2,
Line 27, "of *Azalea* based on my observations" should read
-- of *Azalea* based on observations --.

Column 4,
Line 24, "to growth through the summer" should read
-- to grow through the summer --.

Line 31, "with spreading while glandular hairs." should read
-- with spreading white glandular hairs. --.

UNITED STATES PATENT AND TRADEMARK OFFICE

CERTIFICATE OF CORRECTION

PATENT NO. : PP 19,899 P2
APPLICATION NO. : 11/500521
DATED : April 14, 2009
INVENTOR(S) : Amy Duck Thomas It is certified that error appears in the above-identified patent and that said Letters Patent is hereby corrected as shown below:

Line 41, "The calyx is 1/8″ long," should read
-- The calyx is 1/8″ to 1/4″ long, --.

Signed and Sealed this

Seventeenth Day of November, 2009

David J. Kappos

David J. Kappos
*Director of the United States Patent and Trademark Office*